(12) United States Patent
Beaulieu et al.

(10) Patent No.: US 8,239,061 B2
(45) Date of Patent: Aug. 7, 2012

(54) SPECIFIC GRAVITY MONITORING AND SORTING SYSTEM

(76) Inventors: Kelly Beaulieu, Portage la Prairie (CA); Philip Maurice Church, Stittsville (CA)

(*) Notice: Subject to any disclaimer, the term of this patent is extended or adjusted under 35 U.S.C. 154(b) by 624 days.

(21) Appl. No.: 12/513,977

(22) PCT Filed: Oct. 26, 2007

(86) PCT No.: PCT/CA2007/001925
§ 371 (c)(1),
(2), (4) Date: May 7, 2009

(87) PCT Pub. No.: WO2008/055340
PCT Pub. Date: May 15, 2008

(65) Prior Publication Data
US 2010/0023161 A1 Jan. 28, 2010

Related U.S. Application Data

(60) Provisional application No. 60/864,627, filed on Nov. 7, 2006.

(51) Int. Cl.
*G01B 15/00* (2006.01)
*G06F 7/00* (2006.01)
*H01T 19/04* (2006.01)
*G01N 21/84* (2006.01)

(52) U.S. Cl. ........ 700/230; 700/223; 700/224; 264/410; 250/326; 356/446

(58) Field of Classification Search .......... None
See application file for complete search history.

(56) References Cited

U.S. PATENT DOCUMENTS

| | | | |
|---|---|---|---|
| 4,037,970 A * | 7/1977 | Webster et al. | 356/418 |
| 4,186,836 A | 2/1980 | Wassmer et al. | |
| 4,576,071 A | 3/1986 | Rayment | |
| 5,000,569 A | 3/1991 | Nylund | |
| 6,250,471 B1 | 6/2001 | Ruthven et al. | |
| 6,339,727 B1 * | 1/2002 | Ladd | 700/28 |
| 6,646,218 B1 | 11/2003 | Campbell et al. | |
| 6,847,447 B2 * | 1/2005 | Ozanich | 356/326 |

FOREIGN PATENT DOCUMENTS
DE 38 42 098 A1 6/1989

OTHER PUBLICATIONS

Scanlon et al, "Quality evaluation of processing potatoes by near infrared reflectance", Journal of the Science of Food and Agriculture, 79:763-771(1999).

* cited by examiner

*Primary Examiner* — Gene Crawford
*Assistant Examiner* — Yolanda Jones
(74) *Attorney, Agent, or Firm* — Ryan W Dupuis; Kyle R. Satterthwaite; Ade & Company Inc.

(57) ABSTRACT

Objects are sorted according to specific gravity by illuminating the objects with near-infrared light with different wavelengths. Measurement of the light absorbed by each object at the different wavelengths permits a dry matter content of the object to be determined. Specific gravity can then be determined using a predetermined correlation between dry matter content and specific gravity. A sorting mechanism responsive to determination of specific gravity by the controller separates the food objects into at least two different groups corresponding to different specific gravity.

24 Claims, 2 Drawing Sheets

SPECIFIC GRAVITY MONITORING AND SORTING SYSTEM

This application claims priority to U.S. Provisional Application No. 60/864,627, filed Nov. 7, 2006.

FIELD OF THE INVENTION

The present invention relates to a system for rapidly and non-destructively determining specific gravity and sorting food objects according to their food processing requirements. More particularly, the present invention relates to a method and a system of determining the specific gravity of potato French fry strips. The system will allow for the sorting of the fry strips for processing according to customer specifications by specific gravity measurement at several locations in a processing line.

BACKGROUND

Specific gravity or the solids content of potatoes is an important determinant of harvest quality. A processing potato must have a high specific gravity and low sugar content. A high specific gravity results in french fries that have a more desirable mealy texture and flavour, are crisp and absorb less oil during frying compared to fries from potatoes with a lower dry matter content. Determining the specific gravity is necessary because it indicates how much water must be evaporated from the potato during the dehydration process prior to frying the strips. It is actually a measure of the dry matter or "solids" in the potato. High specific gravity potatoes make the best French fries and dehydrated potato products. In practice, this attribute of a tuber is an indicator of maturation that the industry uses as a reference to judge fry quality, baking characteristics and storability. More importantly the specific gravity measurements reflect environmental factors and cultural management procedures that were made during the production season. In addition, the distribution of starch or dry matter, sugar content, types of sugars and distribution, internal cell structures, tuber size and shape, tuber defects such as growth cracks and hollow heart can also influence specific gravity measurements. Improper sampling and methods of determinations could mislead specific gravity measurements and result in improper equipment settings on the processing line. This results in product quality losses for the processor.

There is no product or device in existence that can perform automatic monitoring of specific gravity on the french fry processing line. Specific gravity is currently determined by a crude manual method. A sample of tubers and several tubs of water (with salt added to make brine at different specific gravities) are used. The weight in air versus the weight in water method is another of the common methods of specific gravity determinations. Selected sample units are first weighed in air and then the same unit is re-weighed suspended in water. Specific gravity can then be calculated using the following formula:

Specific gravity=Weight in air/(Weight in air−Weight in water)

This is a time-consuming testing method that does not allow for quick and accurate sampling and therefore it does not allow the processor to set the fryers and drier machines in real time. Both sampling methods are also not very accurate as contamination of the brine barrel with dirt, potato starch etc. and contamination of the weighing water occurs after only a few samples have been tested.

The other common method of measuring specific gravity is to use a potato hydrometer. The hydrometer consists of a float with the neck graduated to specific gravity readings. A basket containing the sample is hung beneath the float and the whole assembly placed in water. After some time the float remains steady and the specific gravity is read from where the water level is on the neck of the hydrometer. The higher the specific gravity, the deeper the hydrometer will be in the water.

The disadvantage of this method is that the hydrometer is calibrated to a fixed weight of potatoes in the basket and therefore the sample placed in the basket must be exactly this specified weight.

It can be time consuming finding tubers of the right size to make the exact weight, and also the hydrometer can bob up and down for some time before a reading can be made. If the hydrometer is knocked about, the chart of specific gravity readings inside the neck can be moved, thereby resulting in totally inaccurate readings. Hence, this method, although commonly used, is not thought to be very accurate. A further disadvantage is the sample size: the hydrometer is limited to the amount specified in the basket and therefore is not a very representative sample.

SUMMARY OF THE INVENTION

The proposed concept described herein generally comprises a Near Infra-Red Spectroscopic device that measures the specific gravity of french fry strips in the manufacturing plant. Near infra-red spectrophotometry (NIR) is widely used in the food processing industry for assessing various quality characteristics of food products because it is a rapid, not destructive method that can be adapted for use on processing lines. As described herein, a NIR device has been devised to sample fry strips on the french fry processing line and to allow for the subsequent sorting of the fries by specific gravity to assist the processor in maximizing end-product quality and reducing waste.

According to one aspect of the present invention there is provided a sorting system for sorting food objects according to specific gravity in a processing line, the system comprising:

a conveyor arranged to carry objects therealong;

a near-infrared light source arranged to illuminate objects on the conveyor with near-infrared light in which a first portion of the light has a wavelength readily absorbed by water content in tissues of the object and a second portion of the light has a wavelength absorbed by the water content in tissues of the object less than the first portion;

a detector for measuring light absorbed by the object at the different wavelengths of near-infrared light; and a controller arranged to:

i) determine dry matter content using the light absorbed by the object as measured by the detector; and ii) determine specific gravity using a predetermined relationship between dry matter content and specific gravity.

According to a second aspect of the present invention there is provided a method of sorting food objects according to specific gravity, the method comprising:

illuminating the food objects with near-infrared light in which a first portion of the light has a wavelength readily absorbed by water content in tissues of the object and a second portion of the light has a wavelength less absorbed by the water content in tissues of the object;

measuring light absorbed by each food object at the different wavelengths of near-infrared light; and determining a dry matter content of each food object using the measured light absorbed by the food object; and determining a specific gravity of each food object using a predetermined relationship between dry matter content and specific gravity.

The method preferably includes separating the food objects into at least two different groups corresponding to different ranges of specific gravity.

Preferably the second portion of the near-infrared light has a wavelength readily absorbed by a dry matter portion of the object. More particularly, the second portion of the near-infrared light may have a wavelength readily absorbed by a dry matter portion of a food object comprising a potato product, for example a french fry strip.

As described in the preferred embodiment herein, near-infrared light sources are arranged over the conveyor in which at least a component of the light has a wavelength more sensitive to water absorption than other components of the light. The detector measures the different wavelengths of near-infrared light reflected by the object. A controller is arranged to determine dry matter content in the fry strips by using near infrared (NIR) measurements along with a predetermined calibration of the instrument. The changes in the near-infrared measurements are correlated to the dry matter content of the potato material. The controller is then further arranged to determine specific gravity using a predetermined relationship between dry matter content and specific gravity. A computer controlled system will make a rapid determination of the best route for the fry to travel to produce the best end quality result. Various adjunct driers may be employed to further dry the strips prior to reinstating them onto the conveyor for movement to the frying station.

The conveyor is preferably arranged to carry cut fries therealong in a french fry processing line. The fries are preferably sorted by the controller and a sorting mechanism after a cutting operation of the processing line which cuts potatoes into fries.

There may be provided a surface dryer after the cutting operation and before the near-infrared light source to remove surface moisture on the fries.

The controller and the sorting mechanism may be located after a fryer in the processing line to sort between fries having a specific gravity within an acceptable range from fries having a specific gravity outside of the acceptable range.

Alternatively or additionally, a controller and a sorting mechanism may be located before a fryer in the processing line to sort between fries having a specific gravity within an acceptable range from fries having a specific gravity outside of the range.

The fries outside of the acceptable range may be forwarded to a processing line for a different food object.

The acceptable range preferably includes an upper limit wherein fries are outside of the acceptable range if a specific gravity thereof is above the upper limit.

The acceptable range preferably also includes a lower limit wherein fries are outside of the acceptable range if a specific gravity thereof is below the lower limit.

When the controller and the sorting mechanism sort the fries between those within an acceptable range of specific gravity and those outside of the range, the controller and the sorting mechanism preferably sort the fries within the acceptable range between fries to be sent directly to a fryer and fries to be sent to a dryer before the fryer.

The controller and the sorting mechanism may be provided after the dryer for sorting the fries between an acceptable range to be sent directly to the fryer and fries outside of the acceptable range and arranged to be sent to a second dryer.

The controller and the sorting mechanism may sort the fries after the dryer between fries within an acceptable specific gravity range to be sent to the fryer and fries outside the range arranged to be sent to a reject area.

The sorting mechanism may be actuated by a timer corresponding to a duration for a fry to be displaced by the conveyor from the detector to the sorting mechanism.

The sorting system may be provided in combination with a processing line comprising a plurality of parallel conveyors each having a near-infrared light source, a detector, a controller and a sorting mechanism associated therewith.

The sorting mechanism is preferably responsive to determination of specific gravity by the controller and arranged to separate the food objects into at least two different groups corresponding to different ranges of specific gravity.

The detector may be arranged to measure a length of each food object. In this instance, the sorting mechanism may also be responsive to length determination of the food objects such that the sorting mechanism is arranged to separate the food objects into at least two different groups corresponding to different ranges of lengths.

The detector is preferably arranged to receive multiple reflections along a length of a food object as the food object is displaced along the conveyor. In this instance, the controller may be arranged to identify regions of differing specific gravity along a length of a given food object.

The controller is preferably arranged to identify regions of the given food object having a specific gravity which is lower than a remainder of the given food object.

There may be provided a cutter arranged to remove regions of the given food object having a specific gravity within an unacceptable range of specific gravity.

The wavelength of the near-infrared light from the near-infrared light source is preferably adjustable to correspond to different biotypes of a given food object.

One embodiment of the invention will now be described in conjunction with the accompanying drawings in which:

BRIEF DESCRIPTION OF THE DRAWINGS

In the drawings like characters of reference indicate corresponding parts in the different figures.

DETAILED DESCRIPTION

Figure 1:
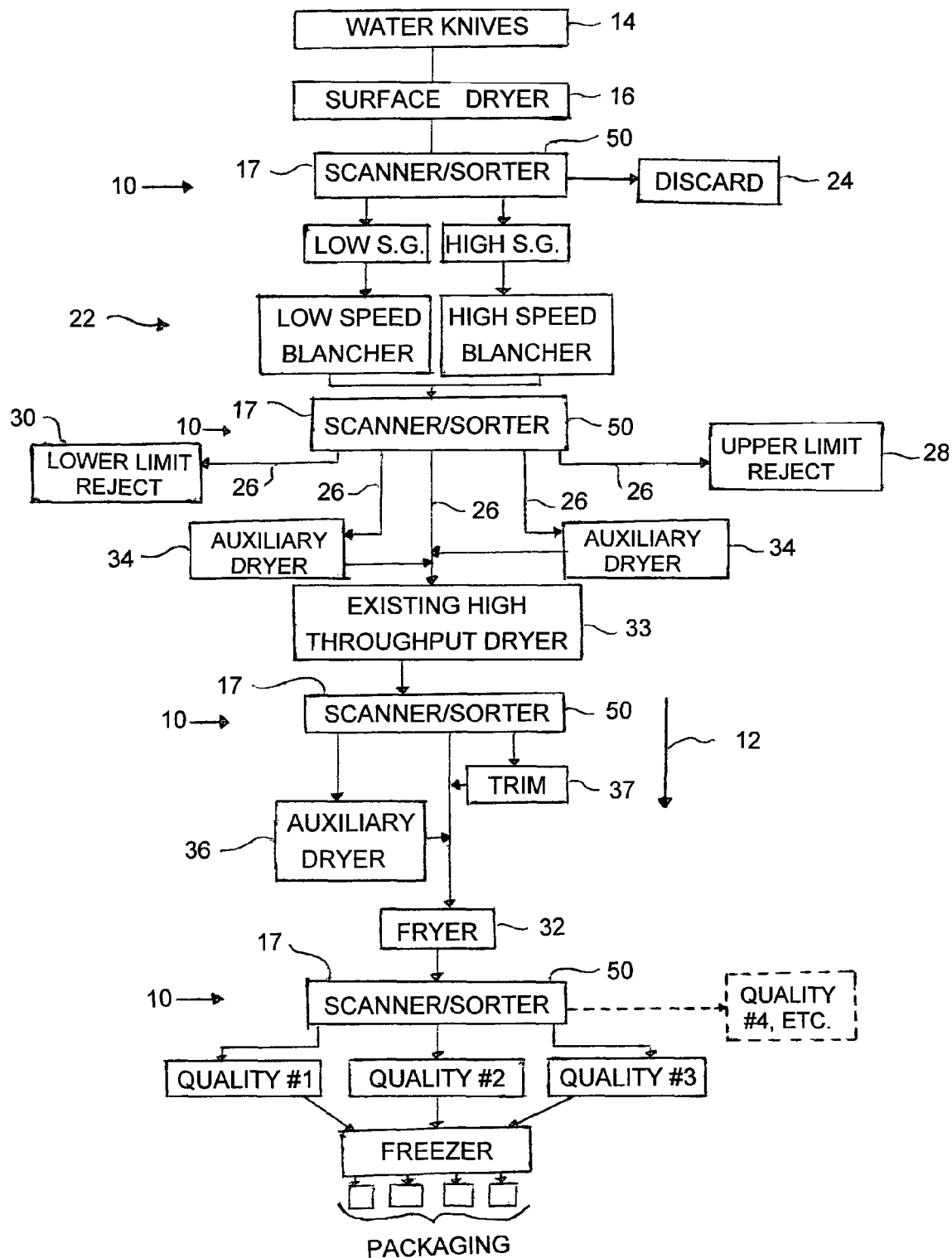
FIG. 1 is an overall schematic view of a food processing line which incorporates the sorting system according to the present invention.
Figure 3:
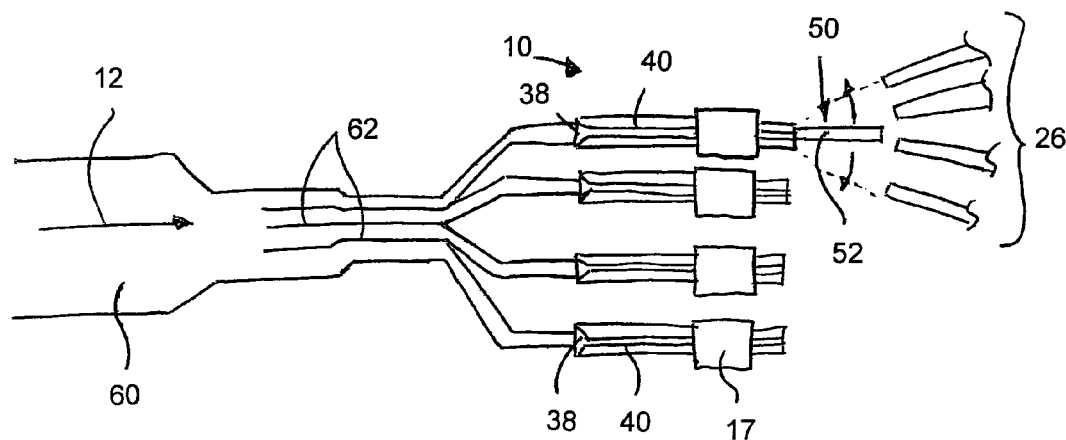
FIG. 3 is a schematic representation of a plurality of sorting systems in parallel with one another for use in the processing line according to FIG. 1.

Referring to the accompanying figures there is illustrated a sorting system generally indicated by reference numeral 10. The system 10 is particularly suited for sorting food objects according to specific gravity. In the exemplary embodiment, the sorting system 10 is applied to a food processing line for sorting food objects, for example french fries, for sorting the fries according to quantities of denser tissues, for example higher dry matter tissues, to determine specific gravity by its correlation to content of water in the tissues versus the content of dry matter in the tissues.

A food processing line 12 is shown in FIG. 1 in which potatoes are first cut into fries at a cutter 14. The cutter 14 comprises a series of wet knives so that the resulting cut fries include surface moisture thereon upon exiting the cutter 14. A surface dryer or air curtain may be required 16 to dry surface moisture, which may affect subsequent scanning operations, so as to improve the effectiveness of the sorting system.

The sorting system generally comprises a scanner 17 for scanning the object and a sorter 50 responsive to the scanner 17. Scanning for denser dry matter tissues in the fries is accomplished using a scanner 17 comprising a near-infrared (NIR) light source 18 which emits NIR light at specific wavelengths and a detector 20 for receiving reflected NIR light back and thereby determine tissue content by assessing what portion of and what wavelengths of the NIR light from the source 18 are absorbed by the food object and which pertain to the water content of the food object.

In the processing line 12 a first scan takes place after the surface dryer or air curtain 16 to initially assess if the cut fries should proceed on to the next step of the process comprising the blancher 22 or if the food objects should be discarded into a reject area 24 or sorted to be sent through various adjunct driers for further drying. Fries will be sent to the reject area if the determined specific gravity thereof falls well outside of the acceptable range which would result in the desired quality of finished products. Depending on if the specific gravity is considered high or low, the fries will be passed through the blancher quickly or more slowly.

The scanner 17 is also arranged to detect start and end points of each fry as it passing along the processing line 12 such that the length of each fry is determined. The sorter 50 responsive to the scanner 17 can thus also be arranged to redirect a fry to the reject area 24 if the length of the fry is outside of a prescribed range of lengths which are considered acceptable, for example if the fry length is below a prescribed lower length limit.

In the illustrated embodiment an additional scanner 17 is placed after the blancher 22 to determine what additional path through the processing line 12 the fry should take to result in a desirable finished product. The scanner 17 after the blancher commands the respective sorter 50 associated therewith to divide the product into subsequent paths 26. For saving floor space, the different paths 26 can be stacked vertically if desired.

The product is directed to the first path if the determined specific gravity is above the upper prescribed limit for the processing system. Accordingly the product is redirected to an upper limit bin 28 to be subsequently forwarded to a different processing line for other potato products having differing specific gravity requirements for product quality.

Similarly another path 26 receives fries redirected thereto if the specific gravity of the fries is determined to be less than a lower limit for acceptable product quality. This path leads to a lower limit bin 30 to be forwarded on similarly to the fries in the upper limit bin 28.

Another path 26 includes fries thereon which have been redirected to the path if their specific gravity is determined to be within an optimum range to be fed directly to a fryer 32 or through an existing high throughput dryer 33 of the processing line before being further sorted or sent to the fryer 32.

The fries are redirected to another of the paths 26 if its specific gravity is below the optimum range to be sent directly to the fryer but is still above the lower prescribed limit of the processing line. In this instance the fries are redirected down the conveyor to a suitable auxiliary dryer 34 which dries the fries to remove excess moisture content and thereby increase the specific gravity thereof to the acceptable range to be sent to the fryer or subsequent scanner. More than one such path to the dryer may be provided if further classification is desired between fries which require only some drying to reach the acceptable range versus some fries which require considerable drying to reach the acceptable range to be sent to the fryer.

In the illustrated embodiment, a further scanner 17 is provided after the dryers 34 when a single drying path is provided so that the scanner after the dryer commands the respective sorter 50 associated therewith to separate the fries between those which have already reached the acceptable limit to be sent to the fryer 32 from those which require further drying. The latter are accordingly sent to a secondary dryer 36 before reaching the acceptable specific gravity range for being subsequently forwarded back to the fryer 32.

Before final processing in the fryer 32, the scanner 17 and sorter 50 just before the fryer may also be arranged to identify regions within individual ones of the fries which have a specific gravity which differs from, for example which is much lower than, an average specific gravity of the remainder of the fry. This is accomplished by taking multiple readings of light reflection from the fry along its length and determining specific gravity at each reading location along the length of the fry. An auxiliary cutter 37 can be operated responsive to the determination of regions of the fries having specific gravity outside of the acceptable range to cut or trim those regions from the remainder. The trimmed parts are then discarded while the remainder continues on to the fryer 32.

A further scanner and sorting system may be positioned after the fryer and before the freezer to sort out those fries that still do not meet the requisite quality parameters specified. Any combination of the sorting and scanning systems may be used by individual processing plants and the units will be custom built to best suit the needs of the processor's clients.

Figure 2:
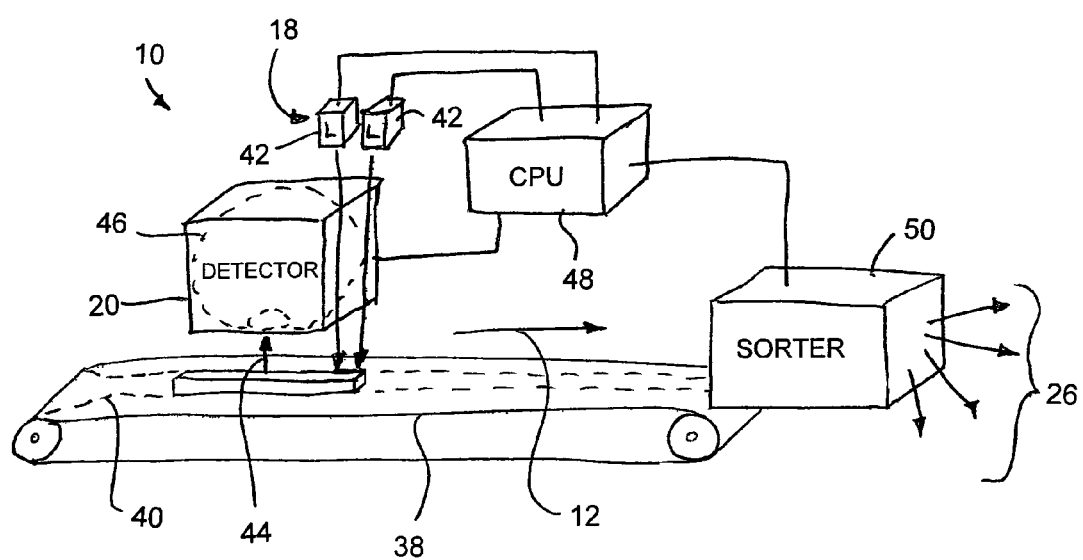
FIG. 2 is a schematic representation of a scanning portion of the sorting system.

Turning now more particularly to FIG. 2, the scanner will now be described in further detail. Each scanner 17 is used in cooperation with a conveyor 38 having suitable guides 40 supported in relation thereto to guide fries so that they are aligned in a longitudinal direction of conveying movement of the conveyor 38. The NIR light source 18 is mounted above the conveyor adjacent one end thereof for directing the NIR light downwardly onto the fries situated on the conveyor 38. The source 18 generally comprises two lasers 42 for emitting NIR light at two respective wavelengths. One of the lasers 42 emits light which has a wavelength which is substantially absorbed by the water content of the tissues of the french fries. The other laser 42 emits light that is less absorbed by the water content and is absorbed by the dry matter of the object and is used as a reference.

The detector 20 of the scanner 17 is also mounted above the conveyor in a common housing with the two lasers of the NIR light source 18. A lens of the detector is positioned close to the object for catching reflections 44 of NIR light from the object. A suitable detector within an integrating sphere 46 is connected to a data acquisition system which is controlled by a processor 48 which controls operations of the system. Multiple scans are taken along the length of the fry as it passes under the source 18 and detector 20. Multiple systems will be required to assess the specific gravity of all the fries traveling in all the conveyor lanes. Multiple lasers and detectors may be positioned inside common housing to reduce the size of the scanning equipment.

The processor determines the dry matter content and accordingly the specific gravity by using the intensity of the reflected light at different wavelengths. The specific gravity is determined using a pre-determined relationship between dry matter content and specific gravity.

The sorter 50, or sorting mechanism, is mounted in association with each scanner 17 in proximity to the respective conveyor 38 for redirecting each fry to the appropriate one of the paths 26 subsequent to scanning the fry using the NIR source 18 and detector 20. The sorter 50 generally comprises a chute 52 which is pivotally mounted adjacent one end of the conveyor. The processor 48 controls the pivotal position of the chute 52 between one of several positions, each comprising the chute 52 being connected in communication between the end of the conveyor 38 and a respective one of the paths 26. The processor 48 includes an integral timer for controlling position of the chute 52 of the sorting mechanism so that the chute is responsive to the determined specific gravity of a fry only once the respective fry reaches the chute 52.

As described herein, the scanner 17 and sorter 50 are useful at various locations as a sorting system within the processing line 12. In the exemplary embodiment scanning and sorting may take place after the cutter 14 once the surface is dry, after the blancher 22 and prior to the fryer 32, after some drying operation to determine if more drying is needed, and finally after the fryer 32 to assess if the desired quality has been reached before the product is released from the processing line 12.

In use the processing line 12 may comprise a plurality of parallel lines, for example up to forty main lines, which initially begin as a single common feed 60 directed by baffles 62 into the individual parallel lines. A sorting system 10 comprising the scanner 17 and sorter 50 are provided in association with each of the separate parallel lines. Each of the sorters 50 may however redirect the fries to several common paths so that all rejected product is redirected to a common reject area 24, all product requiring further drying is sent to a common dryer 34 and all product within the acceptable limits are sent to a common fryer 32.

The technology described herein using NIR is a non-invasive method of determining specific gravity of french fry strips during processing. The system uses spectroscopic methods of analysis to examine the water and plant tissue content of the fry strip. This information is used to make a determination for sorting the fries into different treatment streams and through adjunct driers if required. The sorting equipment, which is part of the system, is controlled by the specific gravity readings generated. The computer makes a determination on each fry strip and moves the fries that require more drying to an adjunct drier. One or more adjunct driers and conveyor systems may be used at the discretion of the processing plant. Fry strips that require further drying prior to moving them back into the stream for frying are put through one of the adjunct driers prior to moving to the fryer. Fries that do not require drying are moved directly to the fryer. Fries that are over or under specific gravity standard requirements go into a separate bin to be recycled into other potato products such as hash browns or dehydrated potato flakes. As many sorting streams as required by the processing plant can be added to the system and accommodated by the specific gravity monitoring system. Each system will be custom built to suit the needs of the plant.

Near-infra red (NIR) instrumentation has been configured to take multiple measurements at specific wavelengths of light reflected from the French fry surface using an integrating sphere. The optical measurements obtained are indicators of the absorption of the NIR light wavelengths and can be used in an algorithm to determine the specific gravity.

The specific gravity monitor (SGM) uses NIR illumination on a sample and measures the reflected light energy with a photodiode detector operating in the NIR region. The sample is illuminated, in turn, by two different NIR wavelengths. The first gets more absorbed by the water content in the potato whereas the second is used as a reference and does not get absorbed as much by the water content, but rather is readily reflected by the object. The detector is fixed to the port of an integrating sphere. The latter offers the benefit to capture light reflected from different angles and to average the signal over the inner reflecting surface of the sphere.

The SGM device is under controlled through the USB port of a computer. Commands are provided to perform automatically a sequence of measurements. Once completed, the data is stored as a record in a data file. A calculation of the total mass (weight) of the fry strips passing through the system will also be provided with the data file.

Once the individual fry strip has been analyzed the computer will determine which sorting treatment to apply. Some fry strips will continue down the main conveyer to the fryer. Other fry strips will be sorted by a mechanical sorting method and moved to another conveyor belt for movement to an adjunct drier. Multiple driers or drier settings can then be used to modify the dry matter and moisture content of the fry strips prior to allowing them to move to the fryer. Determination of the specific gravity may take place in several locations depending on the requirements of the processing plant. For example, four possible locations for specific gravity monitoring devices and associated sorting equipment are immediately after the water knives have cut the strips, after the blancher or prior to the adjunct drier, after the drier and after the fryer. Sorting at each of these locations reduces the variability in product quality.

Commands from the computer will be communicated to PCL controllers to modify the resident times and temperatures of the driers and fryers. This will allow the processor to more precisely control the quality of the fry strips exiting the processing line. The computer can be programmed to automatically adjust the driers and fryers based on the average quality of the product coming into the system.

| Functional Characteristics - Fry Strips | Benefits |
|---|---|
| Device senses specific gravity across length of fry strip (6 to 10 readings per strip in milliseconds) | Allows the processor to set the driers and fryers on line to improve quality of final product |
| Device is not in direct contact with the product | Cleanliness is maintained, device does not need frequent cleaning and is not fouled by product or debris |
| Variation in air humidity in the plant does not affect the device | Moisture in the air will not interfere with accuracy of readings |
| Moisture on the surface of the fries may be removed by a small air jet from an air curtain or surface drier | As the fries leave the water knives excess moisture may need to be removed from the fry surface so that the water does not affect the accuracy of the specific gravity readings |

| Functional Characteristics - Fry Strips | Benefits |
|---|---|
| The device can read at faster than the rate of travel of the individual fries on the conveyor belt. | The conveyor belt is moving at 70 ft per min but the device requires only nanoseconds to take multiple reading and make a sorting determination |
| Sorting the fry strips can easily be accomplished after they have been analysed by the specific gravity monitor | Sorting the strips into separate streams for different treatment by the driers or fryers decreased the variability of the end product |
| Removal of potato strips with specific gravity readings that are too high or too low to be processed into French fries will be directed into a separate bin for use in other potato products | The ability to remove strips with very high or very low specific gravity will greatly enhance the overall quality of the French fry product overall and will result in price premiums to the processor |
| In addition to measuring specific gravity the device will also provide an accurate running total mass (weight) measurement to the processor to indicate total mass of product at any given point requested. | The ability to assess mass will allow the processor to carefully monitor product losses due to moisture loss - these measurements will help in making purchasing decisions and in setting product prices. The mass measurements may also allow the processor to more accurately control oil inputs, and make decisions on other quality parameters in real time. |

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A sorting system for sorting food objects according to specific gravity in a processing line, the system comprising:
    a conveyor arranged to carry objects therealong;
    a near-infrared light source arranged to illuminate objects on the conveyor with near-infrared light in which a first portion of the light has a wavelength readily absorbed by water content in tissues of the object and a second portion of the light has a wavelength absorbed by the water content in tissues of the object less than the wavelength of the first portion of the light;
    a detector for measuring light absorbed by the object at the different wavelengths of near-infrared light; and
    a controller arranged to:
        i) determine dry matter content using the light absorbed by the object as measured by the detector; and
        ii) determine specific gravity using a predetermined relationship between dry matter content and specific gravity.

2. The system according to claim 1 wherein the second portion of the near-infrared light is arranged to have a wavelength readily absorbed by a dry matter portion of the object.

3. The system according to claim 1 wherein the second portion of the near-infrared light is arranged to have a wavelength readily absorbed by a dry matter portion of a food object comprising a potato product.

4. The system according to claim 1 wherein the second portion of the near-infrared light is arranged to have a wavelength readily absorbed by a dry matter portion of a food object comprising a french fry strip.

5. The system according to claim 1 wherein the conveyor is arranged to carry cut fries therealong in a french fry processing line.

6. The system according to claim 5 wherein the fries are arranged to be sorted by the controller and a sorting mechanism after a cutting operation of the processing line which cuts potatoes into fries.

7. The system according to claim 6 wherein there is provided a surface dryer after the cutting operation and before the near-infrared light source to remove surface moisture on the fries.

8. The system according to claim 5 wherein the controller and the sorting mechanism are located after a fryer in the processing line to sort between fries having a specific gravity within an acceptable range from fries having a specific gravity outside of the acceptable range.

9. The system according to claim 5 wherein the controller and the sorting mechanism are located before a fryer in the processing line to sort between fries having a specific gravity within an acceptable range from fries having a specific gravity outside of the range.

10. The system according to claim 9 wherein the fries outside of the acceptable range are forwarded to a processing line for a different food object.

11. The system according to claim 9 wherein the acceptable range includes an upper limit and wherein fries are outside of the acceptable range if a specific gravity thereof is above the upper limit.

12. The system according to claim 9 wherein the acceptable range includes a lower limit and wherein fries are outside of the acceptable range if a specific gravity thereof is below the lower limit.

13. The system according to claim 5 wherein the controller and the sorting mechanism sort the fries between those within an acceptable range of specific gravity and those outside of the acceptable range of specific gravity, and the controller and the sorting mechanism further sort the fries within the acceptable range of specific gravity between fries to be sent directly to a fryer and fries to be sent to a dryer before the fryer.

14. The system according to claim 13 further comprising the controller and the sorting mechanism being provided after the dryer for sorting the fries between those within the acceptable range of specific gravity to be sent directly to the fryer and those outside of the acceptable range of specific gravity to be sent to a second dryer.

15. The system according to claim 13 wherein the controller and the sorting mechanism sort the fries after the dryer between fries within the acceptable range of specific gravity to be sent to the fryer and fries outside of the acceptable range of specific gravity to be sent to a reject area.

16. The system according to claim 1 wherein there is provided a sorting mechanism responsive to determination of specific gravity by the controller and arranged to separate the food objects into at least two different groups corresponding to different ranges of specific gravity.

17. The system according to claim 1 wherein the detector is arranged to measure a length of each food object and wherein there is provided a sorting mechanism responsive to length determination of the food objects such that the sorting mechanism is arranged to separate the food objects into at least two different groups corresponding to different ranges of lengths.

18. The system according to claim 1 wherein the sorting mechanism is actuated by a timer corresponding to a duration for a fry to be displaced by the conveyor from the detector to the sorting mechanism.

19. The system according to claim 1 wherein the detector is arranged to receive multiple reflections along a length of a food object as the food object is displaced along the conveyor.

20. The system according to claim 19 wherein the controller is arranged to identify regions of differing specific gravity along a length of a given food object.

21. The system according to claim 20 wherein the controller is arranged to identify regions of the given food object having a specific gravity which is lower than a remainder of the given food object.

22. The system according to claim 20 wherein there is provided a cutter arranged to remove regions of the given food object having a specific gravity within an unacceptable range of specific gravity.

23. The system according to claim 1 wherein the sorting system is provided in combination with a processing line comprising a plurality of parallel conveyors each having a near-infrared light source, a detector, a controller and a sorting mechanism associated therewith.

24. The system according to claim 1 wherein the wavelength of the near-infrared light from the near-infrared light source is adjustable to correspond to different biotypes of a given food object.

* * * * *